(12) United States Patent
Nickel et al.

(10) Patent No.: US 9,918,865 B2
(45) Date of Patent: Mar. 20, 2018

(54) BRACES USING LACING SYSTEMS

(75) Inventors: Michael J. Nickel, Golden, CO (US);
Sean T. Cavanagh, Golden, CO (US);
Robert E. Burns, Denver, CO (US);
Mark Kerns, Golden, CO (US);
Edward L. Weaver, II, Milford, OH (US); Sherry A. Hinds, Goshen, OH (US); Beth E. Gramza, Cincinnati, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 1005 days.

(21) Appl. No.: 13/174,533

(22) Filed: Jun. 30, 2011

(65) Prior Publication Data
US 2012/0004587 A1 Jan. 5, 2012

Related U.S. Application Data

(60) Provisional application No. 61/360,619, filed on Jul. 1, 2010.

(51) Int. Cl.
*A61F 5/02* (2006.01)
*A61F 5/01* (2006.01)
*A43C 1/00* (2006.01)
*A43C 11/16* (2006.01)

(52) U.S. Cl.
CPC .............. *A61F 5/028* (2013.01); *A43C 1/003* (2013.01); *A43C 11/165* (2013.01); *A61F 5/01* (2013.01); *A61F 5/0118* (2013.01); *A61F 5/0123* (2013.01)

(58) Field of Classification Search
CPC .......... A61F 5/028; A61F 5/01; A61F 5/0118; A61F 5/0123; A43C 1/003; A43C 11/165

USPC .......... 602/5, 23–29, 62, 65, 20–21; 24/712, 24/712.4, 713, 19, 68 R, 68 SK, 71 SK; 128/882; 36/50.1, 117.7; 2/22
See application file for complete search history.

(56) References Cited

U.S. PATENT DOCUMENTS

| | | |
|---|---|---|
| 59,332 A | 10/1866 | White et al. |
| 80,834 A | 8/1868 | Prussia |
| 117,530 A | 8/1871 | Foote |
| 228,946 A | 6/1880 | Schulz |
| 230,759 A | 8/1880 | Drummond |

(Continued)

FOREIGN PATENT DOCUMENTS

| | | |
|---|---|---|
| AT | 127075 | 2/1932 |
| AT | 244804 | 1/1966 |

(Continued)

OTHER PUBLICATIONS

U.S. Appl. No. 09/956,601, filed Sep. 18, 2001, including its prosecution history, Gary R. Hammerslag.

(Continued)

*Primary Examiner* — Ophelia A Hawthorne
(74) *Attorney, Agent, or Firm* — Kevin W. Weber; Sandra K. Nowak

(57) ABSTRACT

The disclosure relates to medical braces having lacing systems for tightening of the medical braces. Some embodiments include multiple components of the lacing system integrated into a single housing piece. For example, multiple reels can be used to tighten different portions of the lacing system, and the multiple reels can be mounted onto a single housing. Also, multiple lace guides can be integrated into, or attached to, a single housing piece.

21 Claims, 14 Drawing Sheets

(56) References Cited

U.S. PATENT DOCUMENTS

| | | |
|---|---|---|
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,393,188 A | 10/1921 | Whiteman |
| 1,469,661 A | 2/1922 | Migita |
| 1,412,486 A | 4/1922 | Paine |
| 1,416,203 A | 5/1922 | Hobson |
| 1,481,903 A | 4/1923 | Hart |
| 1,530,713 A | 2/1924 | Clark |
| 1,502,919 A | 7/1924 | Seib |
| 1,862,047 A | 6/1932 | Boulet et al. |
| 1,995,243 A | 6/1934 | Clarke |
| 2,088,851 A | 8/1937 | Gantenbein |
| 2,109,751 A | 3/1938 | Matthias et al. |
| 2,124,310 A | 9/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,907,086 A | 10/1959 | Ord |
| 2,991,523 A | 7/1961 | Del Conte |
| 3,035,319 A | 5/1962 | Wolff |
| 3,112,545 A | 12/1963 | Williams |
| 3,163,900 A | 1/1965 | Martin |
| 3,169,325 A | 2/1965 | Fesl |
| 3,197,155 A | 7/1965 | Chow |
| 3,221,384 A | 12/1965 | Aufenacker |
| 3,276,090 A | 10/1966 | Nigon |
| 3,401,437 A | 9/1968 | Christpohersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,934,346 A | 1/1976 | Sasaki et al. |
| 3,975,838 A | 8/1976 | Martin |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,408,403 A | 10/1983 | Martin |
| 4,433,456 A | 2/1984 | Baggio |
| 4,463,761 A | 8/1984 | Pols et al. |
| 4,480,395 A | 11/1984 | Schoch |
| 4,507,878 A | 4/1985 | Semouha |
| 4,551,932 A | 11/1985 | Schoch |
| 4,555,830 A | 12/1985 | Petrini et al. |
| 4,574,500 A | 3/1986 | Aldinio et al. |
| 4,616,524 A | 10/1986 | Biodia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,870,723 A | 10/1989 | Pozzobon et al. |
| 4,870,761 A | 10/1989 | Tracy |
| 4,884,760 A | 12/1989 | Baggio et al. |
| 4,937,953 A | 7/1990 | Walkhoff |
| 4,961,544 A | 10/1990 | Biodia |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | De Bortoli |
| 5,065,481 A | 11/1991 | Walkhoff |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,249,377 A | 10/1993 | Walkhoff |
| 5,259,094 A | 11/1993 | Zepeda |
| 5,315,741 A | 5/1994 | Debberke |
| 5,319,868 A | 6/1994 | Hallenbeck |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,381,609 A | 1/1995 | Hieblinger |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| 5,502,902 A | 4/1996 | Sussmann |
| 5,511,325 A | 4/1996 | Hieblinger |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,658,241 A * | 8/1997 | Deharde et al. .......... 602/5 |
| 5,669,116 A | 9/1997 | Jungkind |
| 5,718,021 A | 2/1998 | Tatum |
| 5,718,065 A | 2/1998 | Locker |
| 5,732,483 A | 3/1998 | Cagliari |
| 5,736,696 A | 4/1998 | Del Rosso |
| 5,737,854 A | 4/1998 | Sussmann |
| 5,755,044 A | 5/1998 | Veylupek |
| 5,761,777 A | 6/1998 | Leick |
| 5,784,809 A | 7/1998 | McDonald |
| 5,819,378 A | 10/1998 | Doyle |
| 5,934,599 A | 8/1999 | Hammerslag |
| 5,956,823 A | 9/1999 | Borel |

(56) References Cited

U.S. PATENT DOCUMENTS

| | | |
|---|---|---|
| 6,038,791 A | 3/2000 | Cornelius et al. |
| 6,070,886 A | 6/2000 | Cornelius et al. |
| 6,070,887 A | 6/2000 | Cornelius et al. |
| 6,052,921 A | 8/2000 | Oreck |
| 6,102,412 A | 8/2000 | Staffaroni |
| D430,724 S | 9/2000 | Matis et al. |
| 6,119,318 A | 9/2000 | Maurer |
| 6,128,836 A | 10/2000 | Thierry |
| 6,148,489 A | 11/2000 | Dickie et al. |
| 6,202,953 B1 | 3/2001 | Hammerslag |
| 6,213,968 B1 | 4/2001 | Heinz et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,289,558 B1 | 9/2001 | Hammerslag |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,543,159 B1 | 4/2003 | Carpenter et al. |
| 6,568,103 B2 | 5/2003 | Durocher |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,802,439 B2 | 10/2004 | Azam et al. |
| 6,877,256 B2 | 4/2005 | Martin et al. |
| 6,922,917 B2 | 8/2005 | Kerns et al. |
| 6,945,543 B2 | 9/2005 | De Bortoli et al. |
| 6,976,972 B2 | 12/2005 | Bradshaw |
| 6,993,859 B2 | 2/2006 | Martin et al. |
| D521,226 S | 5/2006 | Douglas et al. |
| 7,076,843 B2 | 7/2006 | Sakabayashi |
| 7,082,701 B2 | 8/2006 | Dalgaard et al. |
| 7,134,224 B2 | 11/2006 | Elkington et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,367,522 B2 | 5/2008 | Chen |
| 7,442,177 B1 | 10/2008 | Garelick |
| 7,584,528 B2 | 9/2009 | Hu |
| 7,591,050 B2 | 9/2009 | Hammerslag |
| 7,597,675 B2 | 10/2009 | Ingimundarson et al. |
| 7,617,573 B2 | 11/2009 | Chen |
| 7,694,354 B2 | 4/2010 | Philpott et al. |
| 7,908,769 B2 | 3/2011 | Pellegrini |
| 7,950,112 B2 | 5/2011 | Hammerslag et al. |
| 7,954,204 B2 | 6/2011 | Hammerslag et al. |
| 7,992,261 B2 | 8/2011 | Hammerslag et al. |
| 8,056,150 B2 | 11/2011 | Stokes et al. |
| 2002/0068890 A1 | 6/2002 | Schwenn et al. |
| 2002/0095750 A1 | 7/2002 | Hammerslag |
| 2002/0178548 A1 | 12/2002 | Freed |
| 2003/0177662 A1 | 9/2003 | Elkington et al. |
| 2005/0054960 A1 | 3/2005 | Telles et al. |
| 2005/0081403 A1 | 4/2005 | Mathieu |
| 2005/0098673 A1 | 5/2005 | Huang |
| 2005/0198866 A1 | 9/2005 | Wiper et al. |
| 2006/0156517 A1 | 7/2006 | Hammerslag |
| 2007/0169378 A1 | 7/2007 | Soderberg |
| 2008/0016717 A1 | 1/2008 | Ruban |
| 2008/0060167 A1 | 3/2008 | Hammerslag |
| 2008/0060168 A1 | 3/2008 | Hammerslag |
| 2008/0066272 A1* | 3/2008 | Hammerslag et al. ......... 24/712 |
| 2008/0249448 A1 | 10/2008 | Stevenson |
| 2009/0184189 A1 | 7/2009 | Soderberg |
| 2010/0139057 A1 | 6/2010 | Soderberg |
| 2010/0299959 A1 | 12/2010 | Hammerslag |
| 2011/0167543 A1 | 7/2011 | Kovacevich et al. |
| 2011/0225843 A1 | 9/2011 | Kerns et al. |
| 2011/0266384 A1 | 11/2011 | Goodman et al. |

FOREIGN PATENT DOCUMENTS

| | | |
|---|---|---|
| CA | 2112789 | 8/1994 |
| CA | 2114387 | 8/1994 |
| CH | 41765 | 11/1908 |
| CH | 111341 | 11/1925 |
| CH | 199766 | 9/1938 |
| CH | 204834 | 5/1939 |
| DE | 555211 | 7/1932 |
| DE | 641976 | 2/1937 |
| DE | 1661668 | 8/1953 |
| DE | 7043154 | 3/1971 |
| DE | 7045778 | 3/1971 |
| DE | 1785220 | 5/1971 |
| DE | 2062795 | 6/1972 |
| DE | 7047038 | 1/1974 |
| DE | 2341658 | 3/1974 |
| DE | 2414439 | 10/1975 |
| DE | 2900077 | 7/1980 |
| DE | 2914280 | 10/1980 |
| DE | 31 01 952 A1 | 9/1982 |
| DE | 8101488 | 7/1984 |
| DE | 38 13 470 A1 | 11/1989 |
| DE | 3822113 C2 | 1/1990 |
| DE | 43 02 401 A1 | 8/1994 |
| DE | 9413147 | 10/1994 |
| DE | 93 15 776.2 | 2/1995 |
| DE | 9315776 | 2/1995 |
| DE | 29503552 | 4/1995 |
| DE | 19624553 | 1/1998 |
| DE | 19945045 A1 | 9/1999 |
| DE | 20116755 | 1/2002 |
| EP | 0 589 232 A1 | 3/1994 |
| EP | 0 589 233 A1 | 3/1994 |
| EP | 0 614 624 | 9/1994 |
| EP | 0 614 625 A1 | 9/1994 |
| EP | 0 651 954 A1 | 5/1995 |
| EP | 0 693 260 B1 | 1/1996 |
| EP | 0 734 662 A1 | 10/1996 |
| EP | 1 236 412 A | 9/2002 |
| FR | 1349832 | 1/1964 |
| FR | 1374110 | 10/1964 |
| FR | 1404799 | 7/1965 |
| FR | 2019991 | 7/1970 |
| FR | 2108428 | 5/1972 |
| FR | 2173451 | 10/1973 |
| FR | 2175684 | 10/1973 |
| FR | 2 399 811 | 3/1979 |
| FR | 2 565 795 A1 | 12/1985 |
| FR | 2 598 292 A1 | 11/1987 |
| FR | 2 770 379 A1 | 5/1999 |
| FR | 2 814 919 A1 | 4/2002 |
| GB | 11673 | 6/1899 |
| GB | 216400 | 5/1924 |
| GB | 2 449 722 A | 5/2007 |
| JP | 33-9202 | 9/1955 |
| JP | 49-028618 | 3/1974 |
| JP | 51-131978 | 11/1975 |
| JP | 51-002776 | 1/1976 |
| JP | 51-121375 | 10/1976 |
| JP | 53-124987 | 3/1977 |
| JP | 54-108125 | 1/1978 |
| JP | 62-057346 | 4/1987 |
| JP | 63-080736 | 5/1988 |
| JP | 03-031760 | 3/1991 |
| JP | 3030988 | 3/1991 |
| JP | 7-208 | 1/1995 |
| JP | 10-199366 | 7/1998 |
| JP | 2004-016732 | 1/2004 |
| JP | 2004-041666 | 2/2004 |
| WO | WO 94-09728 | 5/1994 |
| WO | WO 1995/03720 | 2/1995 |
| WO | WO 1998/37782 | 9/1998 |
| WO | WO 1999/15043 A1 | 4/1999 |
| WO | 2000-53045 | 9/2000 |
| WO | WO 2000/76337 A1 | 12/2000 |
| WO | WO 2001/08525 A1 | 2/2001 |

(56) References Cited

FOREIGN PATENT DOCUMENTS

| | | |
|---|---|---|
| WO | WO 01/60289 | 8/2001 |
| WO | WO 2007/016983 A1 | 2/2007 |

OTHER PUBLICATIONS

Re-Examination of U.S. Pat. No. 7,591,050, Re-Exam Control No. 90/011,028, including its prosecution history, filed Jun. 11, 2010, Gary R. Hammerslag.
U.S. Appl. No. 13/174,527, dated Jun. 30, 2011, Jesse D. Cotterman, et al.
U.S. Appl. No. 13/273,060, dated Oct. 13, 2011, Soderberg, et al.
ASOLO® Boot Brochure Catalog.

\* cited by examiner

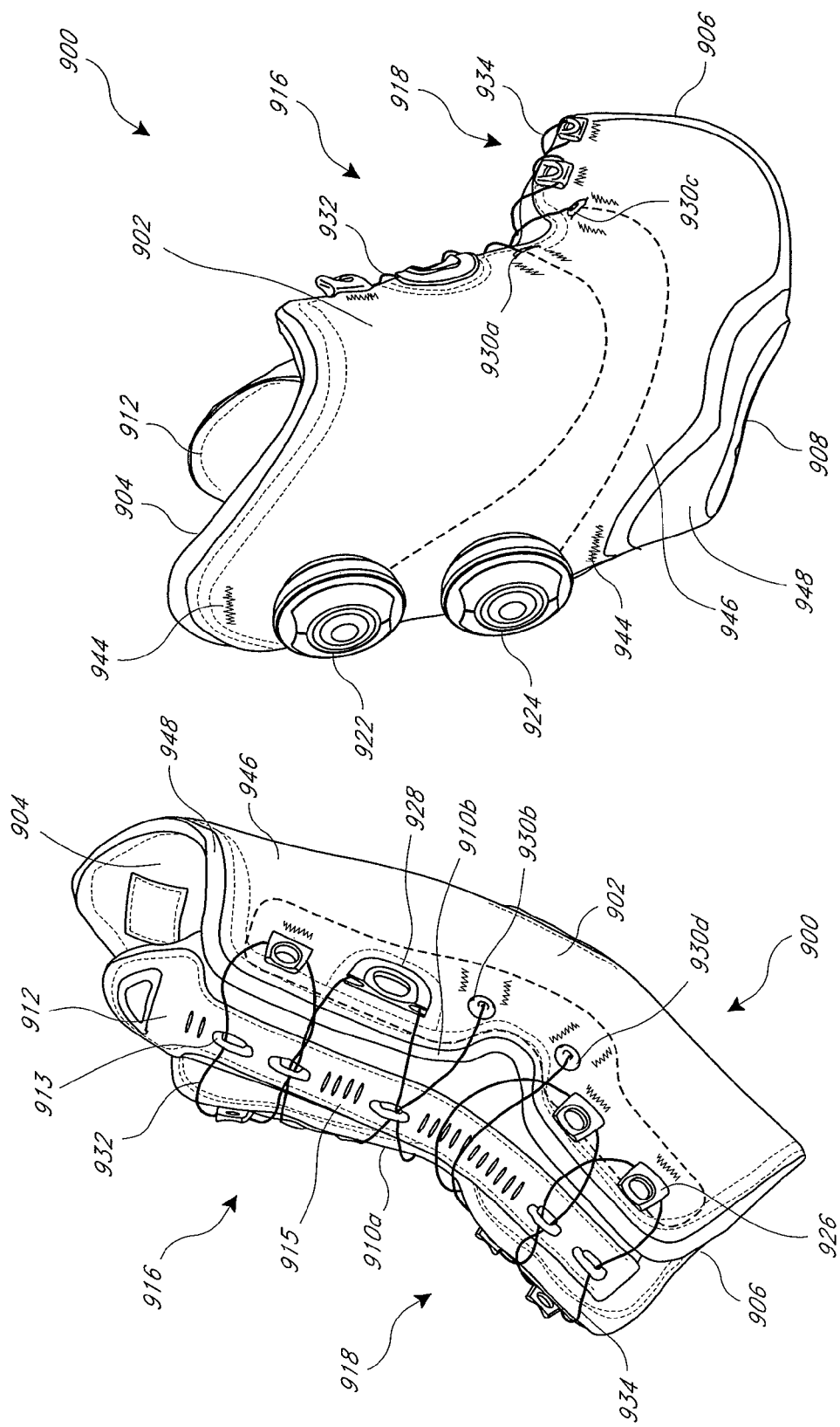

BRACES USING LACING SYSTEMS

CROSS-REFERENCE TO RELATED APPLICATIONS

This application claims priority under 35 U.S.C. § 119(e) to U.S. Provisional Application No. 61/360,619, filed on Jul. 1, 2010, and titled "BRACES USING LACING SYSTEMS," the entirety of which is hereby incorporated by reference herein and made a part of this specification for all that it discloses.

BACKGROUND OF THE INVENTION

Field of the Invention

Embodiments of the present invention relate to medical braces (e.g., wrist braces and ankle braces), and more particularly to medical braces that use lacing systems.

Description of the Related Art

Although various lacing systems are available for use in connection with various wearable articles including medical braces, there remains a need for improvement.

SUMMARY OF THE INVENTION

By way of example and not limitation, a medical brace can include a main body configured to be worn by a user and a lacing system configured to tighten and loosen the main body. The lacing system can include a first reel configured to rotate about a first axis to tighten a first portion of the lacing system, a second reel configured to rotate about a second axis different than the first axis to tighten a second portion of the lacing system, and a housing piece configured to house both the first reel and the second reel.

The housing piece can be substantially rigid and can be configured to provide substantially rigid support to the medical brace. In some embodiments, the medical brace does not include any rigid support member other than the housing piece. The second reel can be positioned adjacent to the first reel. The medical brace can be a wrist brace. The medical brace can be an ankle brace.

The lacing system can further include a plurality of lace guides mounted onto a second housing piece. The second housing piece can be substantially rigid and configured to provide substantially rigid support to the medical brace. In some embodiments, the medical brace does not include any rigid support member other than the housing piece and the second housing piece.

The medical brace can include a first side and a second side that are configured to be drawn together by tightening the lacing system. The first reel and second reel can be positioned on the first side of the medical brace, and the plurality of lace guides mounted onto the second housing piece can be positioned on the second side of the medical brace.

The medical brace can include an upper layer, wherein the first reel and the second reel are positioned above the upper layer, and wherein the housing piece is positioned under the upper layer. The upper layer can include a first hole and a second hole, and the first reel can extend through the first hole and the second reel can extend through the second hole.

A medical brace can include a main body configured to be worn by a user; and a lacing system configured to tighten and loosen the main body. The lacing system can include a lace, a plurality of lace guides configured to provide a lace path for the lace, and a unitary housing piece supporting the plurality of lace guides. A first guide of the plurality of lace guides can have a first opening and a second opening and a lace channel extending between the first opening and the second opening, a second guide of the plurality of lace guides can have a first opening, a second opening, and a lace channel extending between the first opening and the second opening, and the second opening of the first guide and the first opening of the second guide can be positioned between the first opening of the first guide and the second opening of the second guide. The housing piece can be substantially rigid and can be configured to provide substantially rigid support to the medical brace.

In some embodiments, the medical brace does not include any rigid support member other than the housing piece.

The medical brace can include a first side and a second side that are configured to be drawn together by tightening the lacing system. The plurality of lace guides supported by the unitary housing piece can be positioned on the first side of the medical brace. In some embodiments, no additional lace guides are positioned on the first side of the medical brace.

The plurality of lace guides supported by the unitary housing piece can be spaced apart from each other with portions of the unitary housing piece extending between the lace guides. The plurality of lace guides supported by the unitary housing piece can be arranged generally linearly along a side of the medical brace.

The medical brace can include an upper layer, and the plurality of lace guides can be positioned above the upper layer, while the unitary housing piece can be positioned under the upper layer.

The upper layer can include a plurality of holes corresponding to the plurality of lace guides, and the lace guides can extend through the holes in the upper layer.

BRIEF DESCRIPTION OF THE DRAWINGS

Various embodiments are depicted in the accompanying drawings for illustrative purposes, and should in no way be interpreted as limiting the scope of the inventions.

FIG. 9 is a perspective view of an embodiment of an ankle brace with an embodiment of a lacing system.

FIG. 10 is another perspective view of the ankle brace of FIG. 9.

DETAILED DESCRIPTION OF THE PREFERRED EMBODIMENTS

Figure 1:
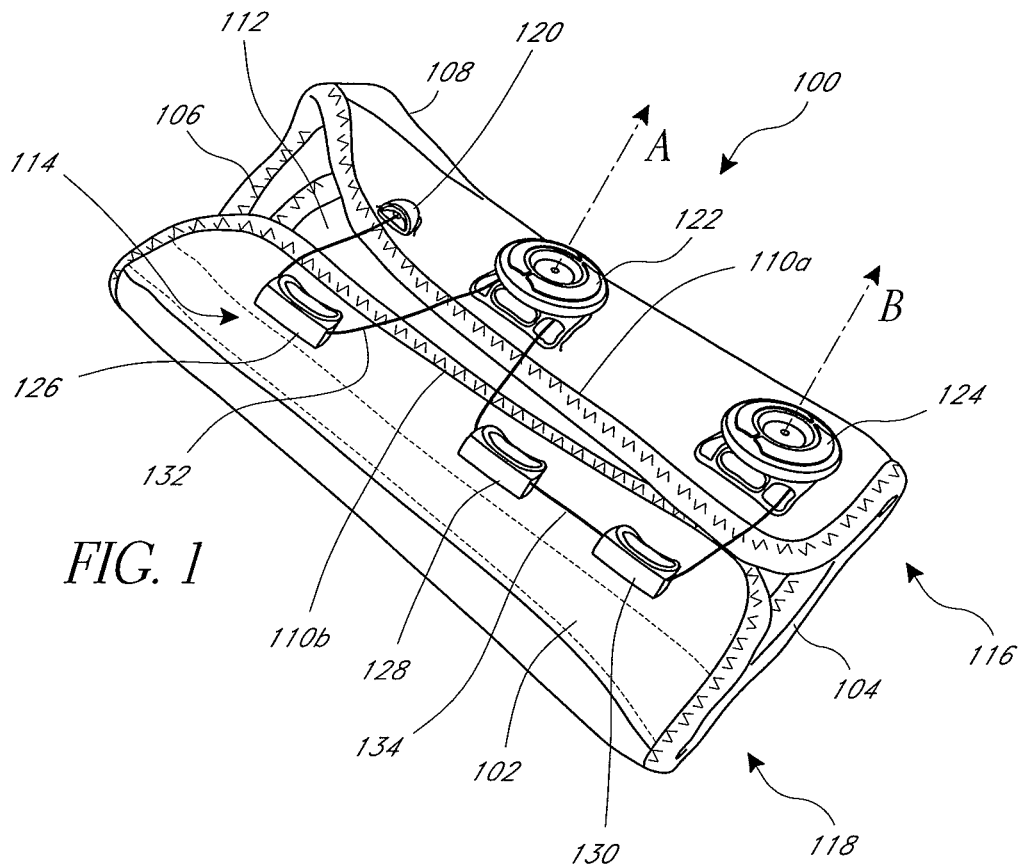
FIG. 1 is a perspective view of an embodiment of a wrist brace with an embodiment of a lacing system.

FIG. 1 is a perspective view of a wrist brace 100. The illustrated wrist brace is configured to be used on a left wrist of the wearer, but a similar brace could be made for use on the right wrist by rearranging and modifying the features of the wrist brace 100. Although the illustrated embodiment is a wrist brace, it will be understood that similar features can be incorporated into various other braces or even into other articles such as, but not limited to, hats, gloves, boots, shoes, etc.

The brace 100 can have a main body 102 that can be generally cylindrical to receive the wearer's arm therein. The main body 102 can have a main opening 104 that allows the user's arm to enter the main body 102, and a fingers hole 106, and a thumb hole 108 (hidden from view in FIG. 1). The main body 102 can have edges 110a-b separated by a space that can increase or decrease depending on the size of the wearer's arm and to allow the wearer to put the brace on and to remove the brace. A tongue 112 can be positioned between and under the edges 110a-b, and can be secured to the inside of the main body 102, for example, using an elastic material. In some embodiments, the brace 100 can include a rigid support member (hidden from view) configured to maintain the wearer's wrist in the design orientation with relatively little freedom of movement.

The brace 100 can include a lacing system 114 configured to draw the edges 110a-b towards each other to tighten the brace 100 around the wrist of the wearer. The lacing system 114 can include various components, some of which are shown in the illustrated embodiment, but it will be understood that aspects of the example illustrated lacing system 114 can be altered, omitted, or added to in other embodiments. The lacing system 114 can include a first portion 116 on a first side 110a of the brace 100 and a second portion 118 on a second side 110b of the brace 100 (see the phantom lines in FIG. 2). The first portion 116 can include a lace stop 120, a first reel 122, and a second reel 124. The second portion 118 can include three lace guides 126, 128, 130. Other combinations of reels, guides, and stops can be used.

A first lace 132 can start at the lace stop 120, pass through the first lace guide 126, and enter the first reel 122. The reel 122 can be configured to draw the first lace 132 into the reel 122 when a knob of the reel 122 is rotated about a first axis A in the tightening direction. For example, the end of the lace 132 can be tied or otherwise attached to a spool inside the reel 122 such that as the knob and spool rotate in the tightening directions, the lace 132 will be wound around a lace channel such that additional lace 132 is drawn into the reel 122. In some embodiments, the knob of the reel 122 can be rotated in a loosening direction to incrementally release the first lace 132 from the first reel 122. In some embodiments, the reel 122 can be released (e.g., by lifting the knob of the reel 122 to a raised, disengaged position) to allow the lace 132 to be pulled from the reel 122 for loosening. In some embodiments, both releasing actions are possible.

Thus, the reel 122 can be operable to tighten and loosen a front portion (wrist area) of the brace 100 that is associated with the first lace 132.

A second lace 134 can fixedly start at the first reel 122, run through the second lace guide 128, through the third lace guide 130, and to the second reel 124. In the illustrated embodiment, even though the second lace 134 begins at the first reel 122, rotation of the knob of the first reel 122 does not tighten or loosen the second lace 134. Rather, the second lace 134 is merely tied, or otherwise secured, to the first reel 122. When the knob of the second reel 124 is rotated about a second axis B in the tightening direction, the second lace 134 is drawn into the second reel 124. The second lace 134 can be loosened by rotating the knob in the loosing direction in some embodiments, or by transitioning the reel 124 to a disengaged position that releases the second lace 134 for loosening, or both. Thus, the second reel 124 can be operable to tighten and loosen a back portion (forearem area) of the brace 100 that is associated with the second lace 134. In the illustrated embodiment, the axis A is substantially parallel to the axis B, which in some cases can allow the user to rotate both reels 122, 124 with generally the same hand motion without significant reorientation of the brace 100. Other, configurations are possible in which the axis A about which the first reel 122 rotates is not substantially parallel to the axis B about which the second reel 124 rotates. For example, the reels 122, 124 can be located on opposite sides of the brace 100.

Figure 2:
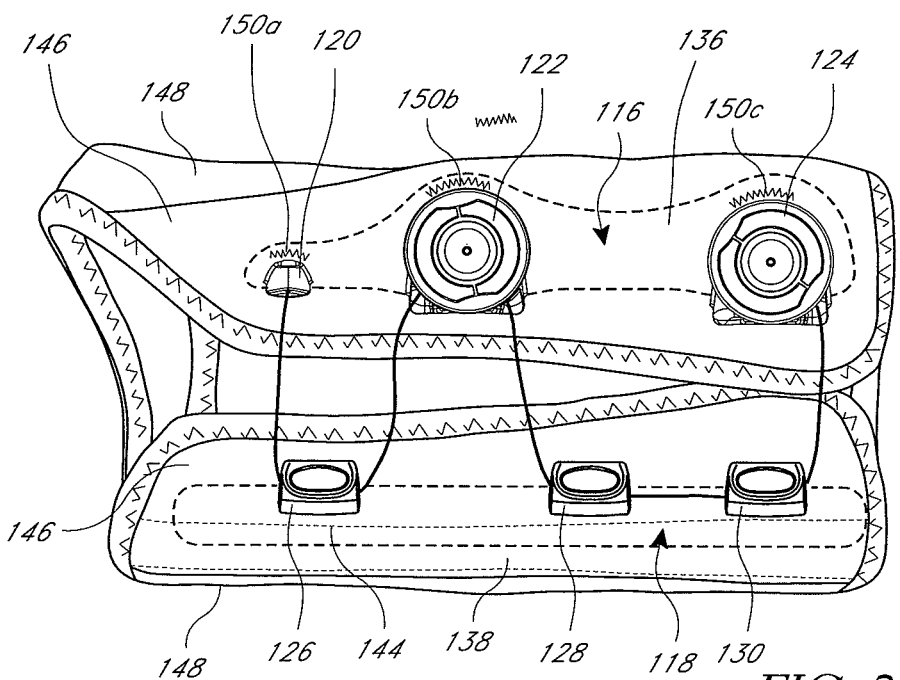
FIG. 2 is another view of the wrist brace of FIG. 1.
Figure 3A:
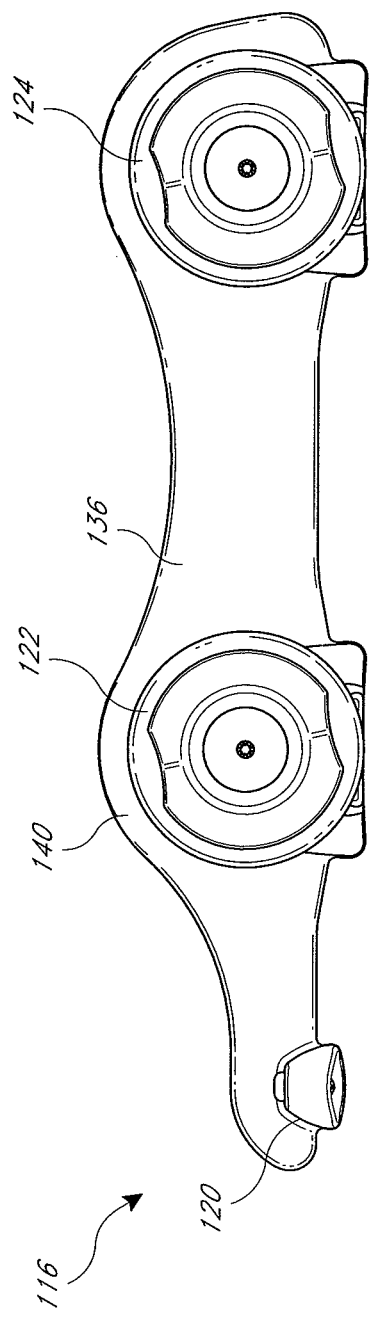
FIG. 3A is a top view of a first portion of the lacing system of the wrist brace shown in FIG. 1.
Figure 3B:
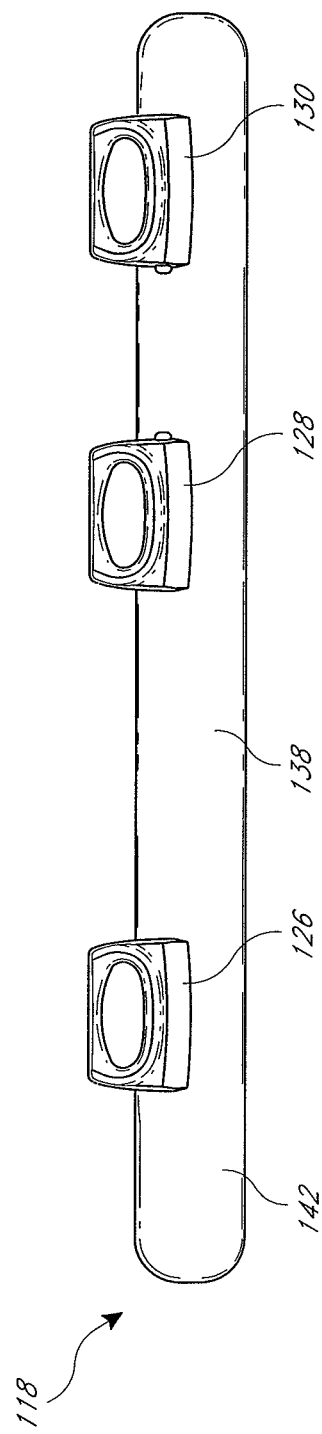
FIG. 3B is a top view of a second portion of the lacing system shown FIG. 1.

In some embodiments, the lace stop 120, first reel 122, and the second reel 124 can all be interconnected or formed as parts of a single first housing piece 136. Similarly, the three lace guides 126, 128, 130 can all be interconnected or formed as parts of a single second housing piece. FIG. 2 is a top view of the wrist brace 100 in which the first housing piece 136 and the second housing piece 138 are shown outlined in dotted lines even though at least a portion of the housing pieces 136, 138 would be hidden from view during normal observation (see FIG. 1). FIG. 3A is a top view of the first portion 116 of the lacing system 114, shown separated from the brace 100. FIG. 3B is a top view of the second portion 118 of the lacing system 114, also shown separated from the brace 100. The first and second housing pieces 136, 138 can include stitch flanges 140, 142 or areas configured to receive stitching to secure the first and second housing pieces 136, 138 to the brace 100. Alternatively, these flanges could be used for adhesive application, RF welding, or insert molding into the main body 102. Turning back to FIG. 2, a stitch line 144 can pass through the upper layer 146 of the brace 100, through the stitch flange 142, and through an underlying layer 148. In some embodiments, the upper layer 146 covers only a part of the brace, leaving part of the underlying layer 148 exposed and visible. In some embodiments, the underlying material 148 can include neoprene, or any other suitable materials. The underlying material 148 can be a multilayer material. Additional stitch lines 150a-c can be used to secure the first housing piece 136 to the brace 100. In some embodiments, a single stitch line can be used for securing the first housing piece to the brace 100 between the upper layer 146 and the underlying layer 148. The upper layer 146 can include holes therein that correspond to the lace stop 120, first reel 122, second reel 124, and the lace guides 126, 128, 130 such that these components of the lacing system can be positioned on the exterior of the brace 100 while the interconnecting housing pieces 136, 138 can be positioned under the upper layer 146, hidden from view.

Joining the lace stop 120, the first reel 122, and the second reel 124 onto a single interconnected housing piece 136 provides the benefit that the brace 100 can be produced more quickly, more reliably, and at less cost. It can be less time consuming and cheaper to mold one housing piece than three separate pieces. During assembly, it can be simpler to properly position a single housing piece to be secured (e.g., by stitching) to the brace 100 than to properly position three separate pieces. Thus, the occurrence of erroneously positioned pieces can be reduced. Because the positions of the components of the lacing system 114 affect the fit of the brace 100 on the wearer's arm, if the components are misplaced, the brace 100 may not fit properly and the wearer's arm may be not protected and/or treated properly by the brace. Also, in some instances, a single stitch line (e.g., 144) can be used instead of multiple stitch lines when multiple components are joined into a single housing piece, further streamlining the assembly process. Additionally, the interconnection of the components may also serve as a therapeutic stiffener for fixation and may be tailored in thickness to achieve a desired stiffness distribution and contour for the desired therapeutic affect.

Figure 4:
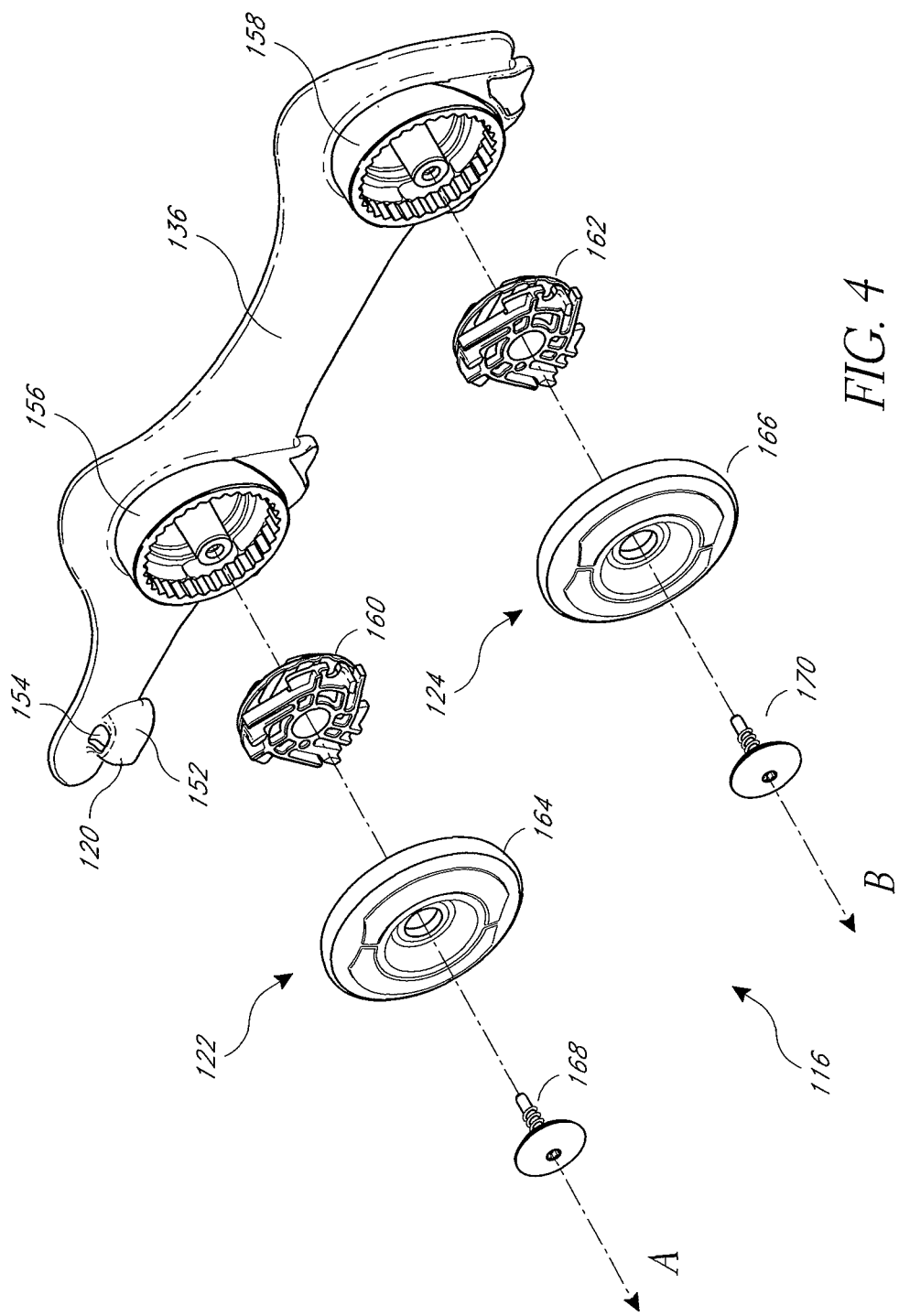
FIG. 4 is an exploded view of the first portion of the lacing system.

Turning now to FIG. 4, which is an exploded perspective view of the first portion 116 of the lacing system 114. The lace stop 120 can be formed as an integral piece with the first housing piece 136. The lace stop 120 can be a generally wedge-shaped structure 152 with a hole 154 formed therethrough. The end of the first lace 132 can be fed through the hole 154 and a knot can be tied or a fitting may be crimped at the end of the first lace 132, thereby preventing the lace 132 from being pulled back through the hole 154.

The first housing piece 136 can include a first reel housing 156 and a second reel housing 158 as integral pieces thereof, or as separate pieces attached thereto. The reel housings 156, 158 can be configured to receive corresponding spool members 160, 162 therein. Knobs 164, 166 can engage the spool member 160, 162, and can be secured to the corresponding reel housings 156, 158 by center screws 168, 170. In the illustrated embodiment, the reels 122, 124 can be configured to incrementally tighten when the knobs 164, 166 are rotated in a tightening direction and to incrementally loosen when the knobs 164, 166 are rotated in a loosening direction. Additional details regarding the reels 122, 124 are disclosed in U.S. application Ser. No. 12/623,362 (the "'362 application"), filed Nov. 20, 2009, and titled REEL BASED LACING SYSTEM, which is hereby incorporated herein by reference in its entirety and made a part of this specification for all that it discloses. Specifically, at least the embodiments shown in FIGS. 3-25 of the '362 application relate to a reel based lacing system configured to incrementally tighten and incrementally loosen.

Although the illustrated embodiment is shown as having reels that incrementally tighten and incrementally loosen, it will be understood that any other suitable type of reel or mechanism for tightening the lace of a lacing system can be used. Other reel designs that may be used in connection with the reels 122, 124 are disclosed in U.S. Provisional patent application Ser. No. 13/098,276 (the "'276 application"), filed Apr. 29, 2011, and titled REEL BASED LACING SYSTEM, which is hereby incorporated herein by reference in its entirety and made a part of this specification for all that it discloses, as well as in U.S. patent application Ser. No. 11/842,013 (the "'013 application"), filed Aug. 20, 2007, titled REEL BASED CLOSURE SYSTEM, published as Publication No. 2008/0066346 on Mar. 20, 2008, which is hereby incorporated herein by reference in its entirety and made a part of this specification for all that it discloses.

Figure 5:
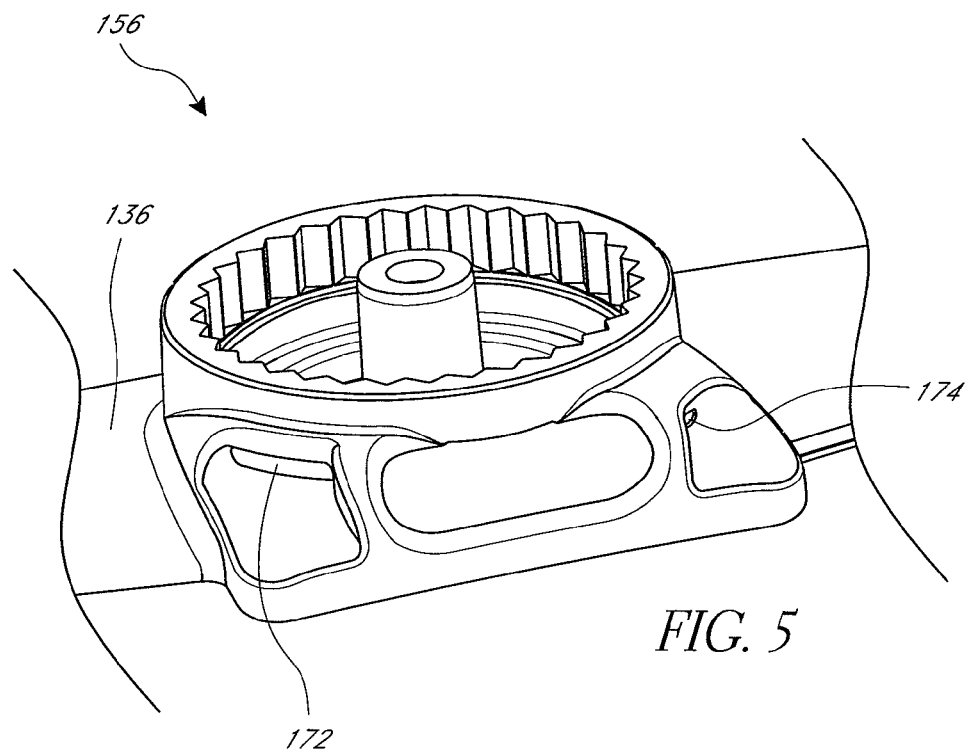
FIG. 5 is a perspective view of a first reel housing.

FIG. 5 is a close-up perspective view of the reel housing 156. The end of the first lace 132 can enter into the reel housing 156 through the hole 172. The hole 172 can be an elongate slot type hole such that the lace 132 can enter the hole 172 from a range of directions without being forced to turn a sharp corner by the walls of the hole 172. The first lace 132 can be attached to the spool member 160 such that when the spool member 160 and knob 164 rotate, the lace 132 is either pulled into the reel housing 156 or driven out of the reel housing 156 via the hole 172.

The end of the second lace 134 can be secured to the reel housing 156 via the hole 174. The lace 134 can be inserted through the hole 174 and a knot can be tied or a fitting may be crimped to the end of the lace 134 such that the lace cannot be pulled back through the hole 174. The second lace 134 merely uses the first reel 122 as a lace stop, and is not drawn into the reel housing 156 when the reel 122 is tightened.

Figure 6:
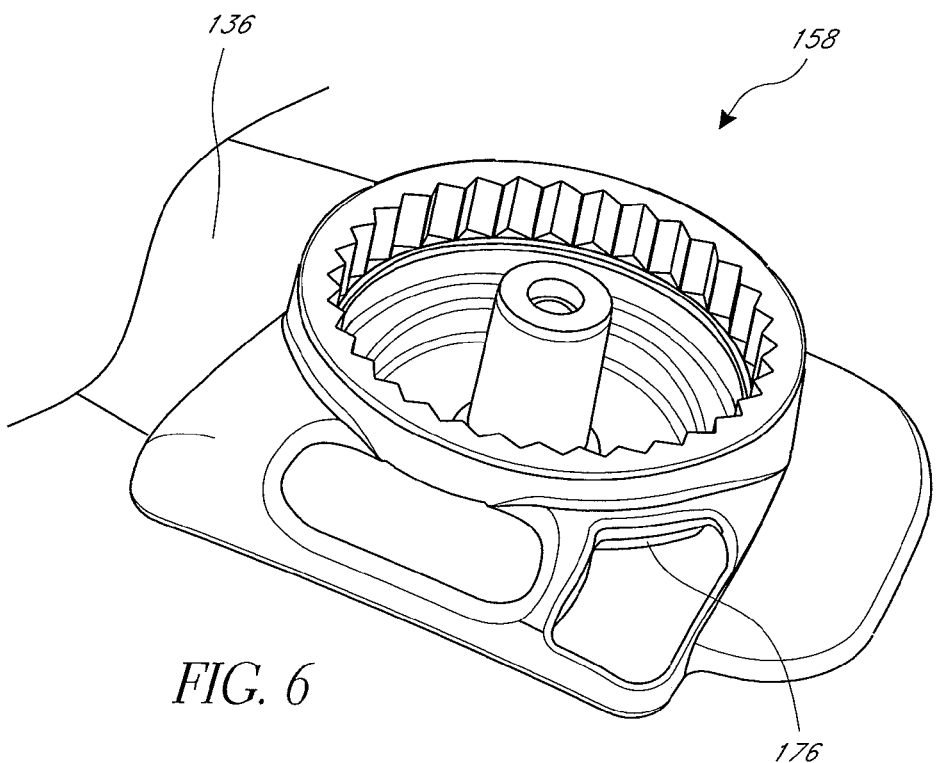
FIG. 6 is a perspective view of a second reel housing.

FIG. 6 is a close-up perspective view of the reel housing 158. The end of the second lace 134 can enter into the reel housing 158 through the hole 176. The hole 176 can be an elongate slot type hole such that the lace 134 can enter the hole 176 from a range of directions without being forced to turn a sharp corner by the walls of the hole 176. The second lace 134 can be attached to the spool member 162 such that when the spool member 162 and knob 166 rotate, the lace 134 is either pulled into the reel housing 158 or driven out of the reel housing 158 via the hole 176. As can be seen, for example, in FIGS. 1 and 2, in some embodiments, the lace 134 can enter the side of the reel 124 that is furthest toward the back of the brace 100 so that the when the reel 124 is tightened, the back end of the brace 100 can be made to fit sufficiently firm on the wearer's arm.

Figure 7:
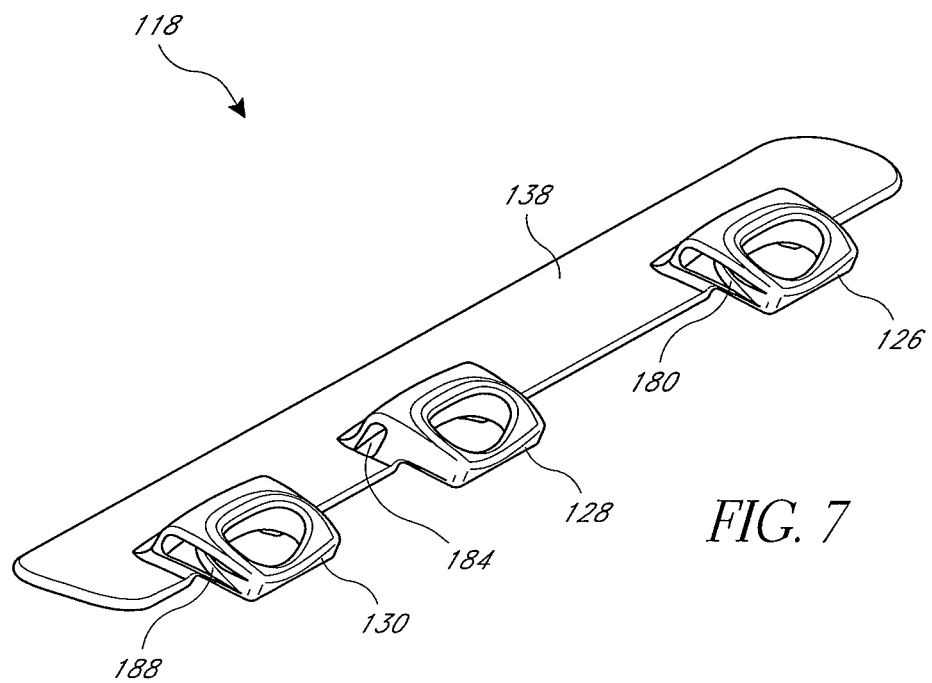
FIG. 7 is a perspective view of the second portion of the lacing system.
Figure 8:
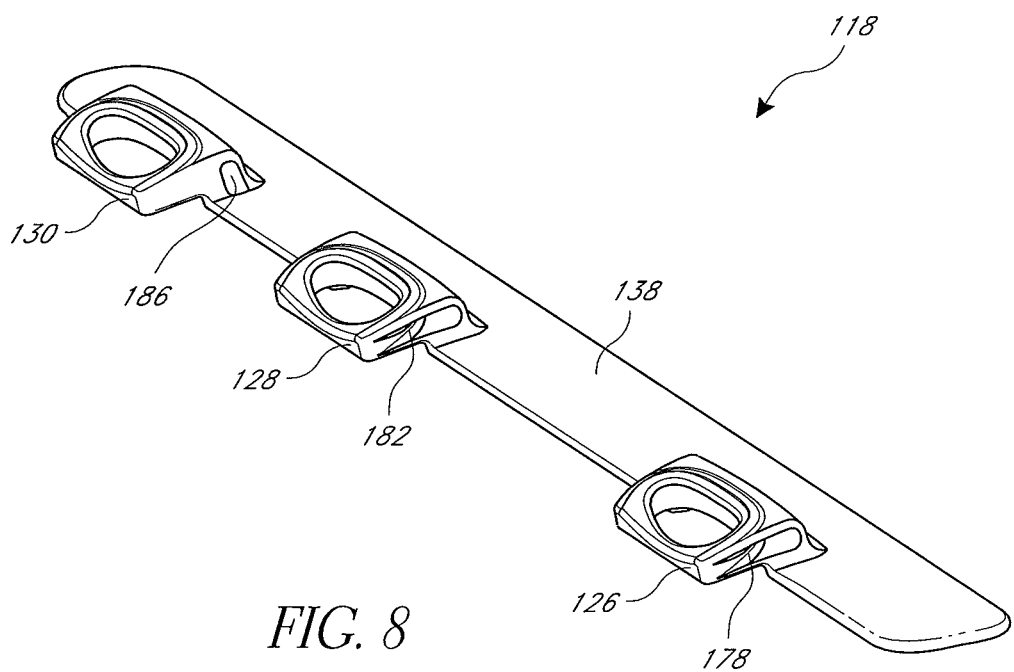
FIG. 8 is another perspective view of the second portion of the lacing system.

FIG. 7 is a perspective view of the second portion 118 of the lacing system 114. FIG. 8 is another perspective view of the second portion 118 of the lacing system 114. In some embodiments, the lace guides 126, 128, 130 can be integrally formed as part of the second housing piece 138. The lace guides 126, 128, 130 can be separately formed and attached to the second housing piece 138 by a fastener or an adhesive or any suitable manner of attachment. The lace guides 126, 128, 130 can be closed back lace guides, although open back lace guides may also be used. The lace guides 126, 128, 130 can be specially positioned on the second housing piece 138 at locations that correspond to the lace path associated with the reels 122, 124 and the lace stop 120. Also, as can be seen by comparing FIGS. 7 and 8 to FIGS. 1 and 2, which show the lacing pattern, the sides of the lace guides 126, 128, 130 can be configured according to the anticipated lace path through the lace guides 126, 128, 130. The lace guide 126 has a first curved exit path 178 on a first side to receive the lace coming from the lace stop 120, and a second curved exit path 180 on the other side to receive lace coming from the reel 122. The lace guide 128 can have a curved exit path 182 on a first side to receive lace from the reel 122, and a hole 184 that points generally toward the lace guide 130 to direct the lace toward the lace guide 130. The lace guide 130 can have a hole 186 than can align collinearly with the hole 184 to receive the lace from the guide 128, and a curved exit path 188 on the opposite side of the hole 186. The curved exit paths 178, 180, 182, and 188 and the holes 184, 186 can provide a lace path that includes no corners of less than about a 3 mm radius, or no corners of less than about a 7 mm radius, or no corners of less than about a 10 mm radius, although curvatures outside of these ranges are also possible.

Many variations are possible. For example, in some embodiments a single lace guide can be used in place of the two lace guides 128 and 130. To preserve the lace path shown in FIGS. 1 and 2, for example, the single lace guide that replaces the guides 128 and 130 would need to be about three times the length of the lace guides shown in the illustrated embodiment. It should be understood that the components of the lacing system 114 are merely examples, and components can be rearranged or omitted and additional components can be added. In another arrangement, loops of webbing could be preassembled to the interconnection flange 138 to provide a soft and low profile guiding element for the lace. This preassembly could be via rivets, stitching, insert molding or other fastening means.

In some embodiments, the first housing piece 136 and/or the second housing piece 138 can provide support or structure to the brace 100. In some embodiments, a substantially rigid or semi-rigid material can be used for the housing piece 136 and/or 138. A hardness in the range of about 40 Shore D to about 85 Shore D would provide this range of stiffness although other hardnesses may be used. The first housing piece 136 and/or the second housing piece 138 can be used in conjunction with a conventional support member (e.g., positioned under the wrist on a wrist brace) or in place of the conventional support member to restrict movement of the wearer's arm. Thus, in some embodiments the conventional support member commonly used in wrist braces can be omitted from the brace 100 and the first housing piece 136 and/or the second housing piece 138 can provide the rigid support to the brace 100. In some embodiments, the first housing piece 136 and/or the second housing piece 138 can be positioned on the underside of the wrist, generally opposite of their positions in the illustrated embodiment.

In some embodiments, a somewhat flexible and resilient material can be used to form the housing piece 136 and/or 138 to thereby provide structure to the brace 100 without rigidly restricting movement thereof. In some embodiments the first housing piece 136 and/or the second housing piece 138 can be flexible enough to allow the user to bend the portion(s) of the brace 100 that houses the first housing piece 136 and/or the second housing piece 138, but the resilient nature of the material can cause the brace 100 to return to substantially its original position once bending force is released. This stiffness may be controlled via both thickness and hardness. Thicknesses from about 0.7 mm to about 4.0 mm and hardnesses in the range of about 20 Shore D to about 85 Shore D may be employed.

In some embodiments, the housing piece 136 can be made from a single material and can be formed as a single unitary piece. The housing piece 138 can likewise be made from a single material and can be formed as a single unitary piece. In some embodiments, different portions of the housing pieces 136, 138 can be made from different material having different levels of hardness, or other differences in properties. Using the housing piece 138 as an example, the stitch flange 142 can be made from a first material, and the lace guides 126, 128, 130 can be made from a different material, for example, by overmolding the guides 126, 128, 130 onto the stitch flange 142. In some embodiments, the stitch flange 142 can be made from a harder, more rigid material than the lace guides 126, 128, 130. In some cases the stitch flange 142 can be rigid so as to provide support to the brace 100, and in some cases it can be advantageous to form the lace guides 126, 128, 130 from a material that is softer than the outer material of the lace so that friction between the guides and the lace will tend to wear the guides 126, 128, 130 rather than the outer surface of the lace. In some embodiments, the stitch flange 142 can be made from a material that is softer than the lace guides 126, 128, 130, such as when the stitch flange 142 is configured to be somewhat flexible to allow movement of the brace 100, and/or when the lace guides 126, 128, 130 are formed from a relatively hard material to prevent wearing of the lace guides during use. The housing piece 136 can similarly be made from multiple materials having different properties, such as hardness. For example, the lace stop 120, the first reel housing 156, and/or the second reel housing 158 can be made of a material that is either harder or softer than the material used to form the stitch flange 140.

FIG. 9 is a perspective view of an embodiment of an ankle brace 900. FIG. 10 is another perspective view of the ankle brace 900. The ankle brace 900 can be symmetrical for use on either the right or left foot, or it can be specifically designed for use on either the left or right foot. It will be understood that many of the feature and principles discussed in connection with the ankle brace 900 can also be applied to other braces, for example the wrist brace discussed above, or even to other articles such as, but not limited to, hats, gloves, boots, shoes, etc.

The brace 900 can have a main body 902 that can be generally cylindrical and shaped to receive a foot of a wearer. The main body 902 can have a main opening 904 that allows the user's foot to enter the main body 902, and a toes hole 906, and a heel hole 908. The main body 902 can have edges 910a-b separated by a space that can increase or decrease depending on the size of the wearer's foot and to allow the wearer to put the brace 900 on and to remove the brace 900. A tongue 912 can be positioned between and under the edges 910a-b, and can have a series of tongue guides 913 through which the laces 932, 934 pass to secure the tongue 912 to the main body 902 of the brace 900. The tongue guides 913 can be positioned along a single integrated tongue strip 915 which can be positioned, for example, down the center of the tongue 912. In some embodiments, the brace 900 can include a rigid support member configured to maintain the wearer's foot in the design orientation with relatively little freedom of movement in the wearer's ankle.

The brace 900 can include a lacing system 914 configured to draw the edges 910a-b towards each other to tighten the brace 900 around the foot of the wearer. The lacing system 914 can include various components, some of which are shown in the illustrated embodiment, but it will be understood that aspects of the example illustrated lacing system 914 can be altered, omitted, or added to in other embodiments. The lacing system 914 can include an upper portion 916 configured to use a first lace 932 to tighten an upper portion of the brace 900 around the portion of the user's foot above the heel. The lacing system 914 can include a lower portion 918 configured to use a second lace 934 to tighten a lower portion of the brace 900 around the portion of the user's foot below the heel.

Figure 12:
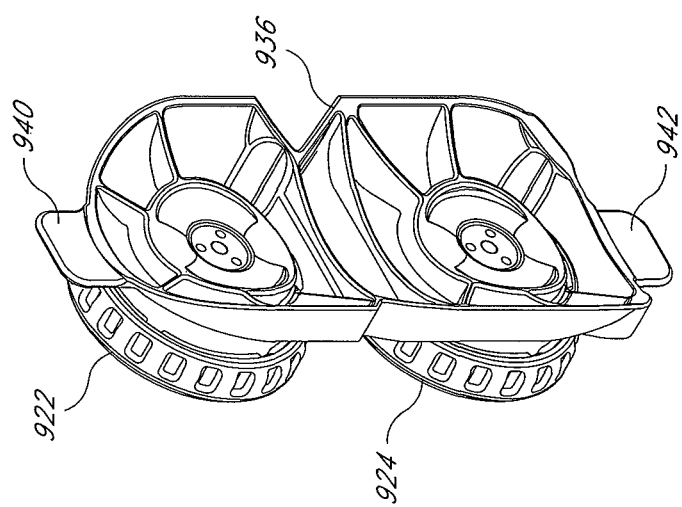
FIG. 12 is another perspective view of the hosing and the two reels.
Figure 11:
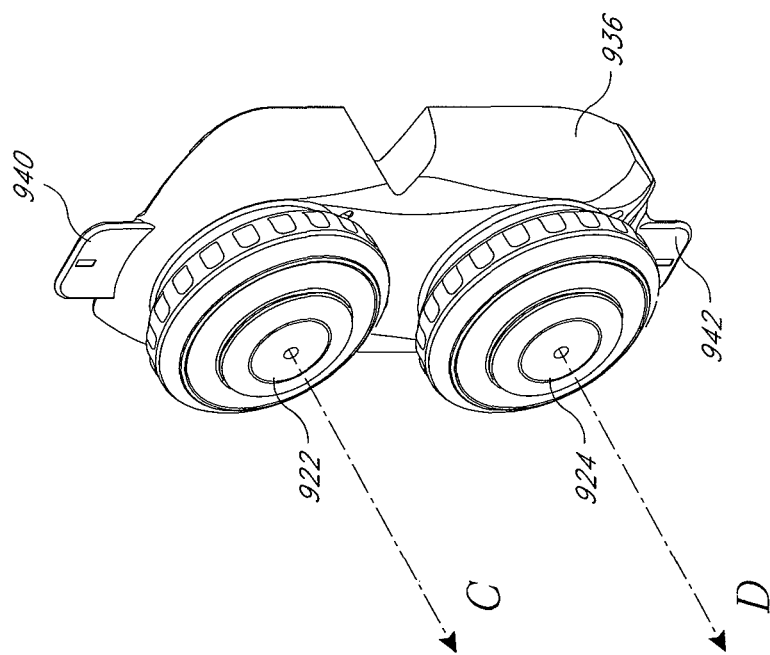
FIG. 11 is perspective view of an example hosing and two reels associated therewith.

As can be seen in FIG. 10, the lacing system 914 can include a first reel 922 configured to gather the first lace 932 therein to tighten the upper portion 916 of the lacing system. The lacing system 914 can also include a second reel 924 configured to gather the second lace 934 therein to tighten the lower portion 918 of the lacing system 914. FIG. 10 shows in dotted lines one possible embodiment of lace paths that lead the laces 932, 934 to the reels 922, 924. In some embodiments, the two reels 922, 924 can both be mounted onto a single housing piece 936. FIG. 11 is a perspective view of the housing piece 936 and the two reels 922, 924 mounted thereto. FIG. 12 is another perspective view of the housing piece 936 and reels 922, 924 showing the back side of the housing piece 936. The housing piece 936 can be substantially rigid or semi-rigid and can provide structure or support to the back of the brace 900. In some embodiments, the rigid housing piece 936 can be used in place of a conventional support member to aid in keeping the wearer's foot in a relatively stable position with little freedom of motion in the user's ankle. This housing piece 936 could also be provisioned with a flange around its periphery to increase the level of support as desired. Positioning multiple reels on a single housing allows greater control of the reels relative to each other and can reduce error and cost during manufacturing.

Figure 13:
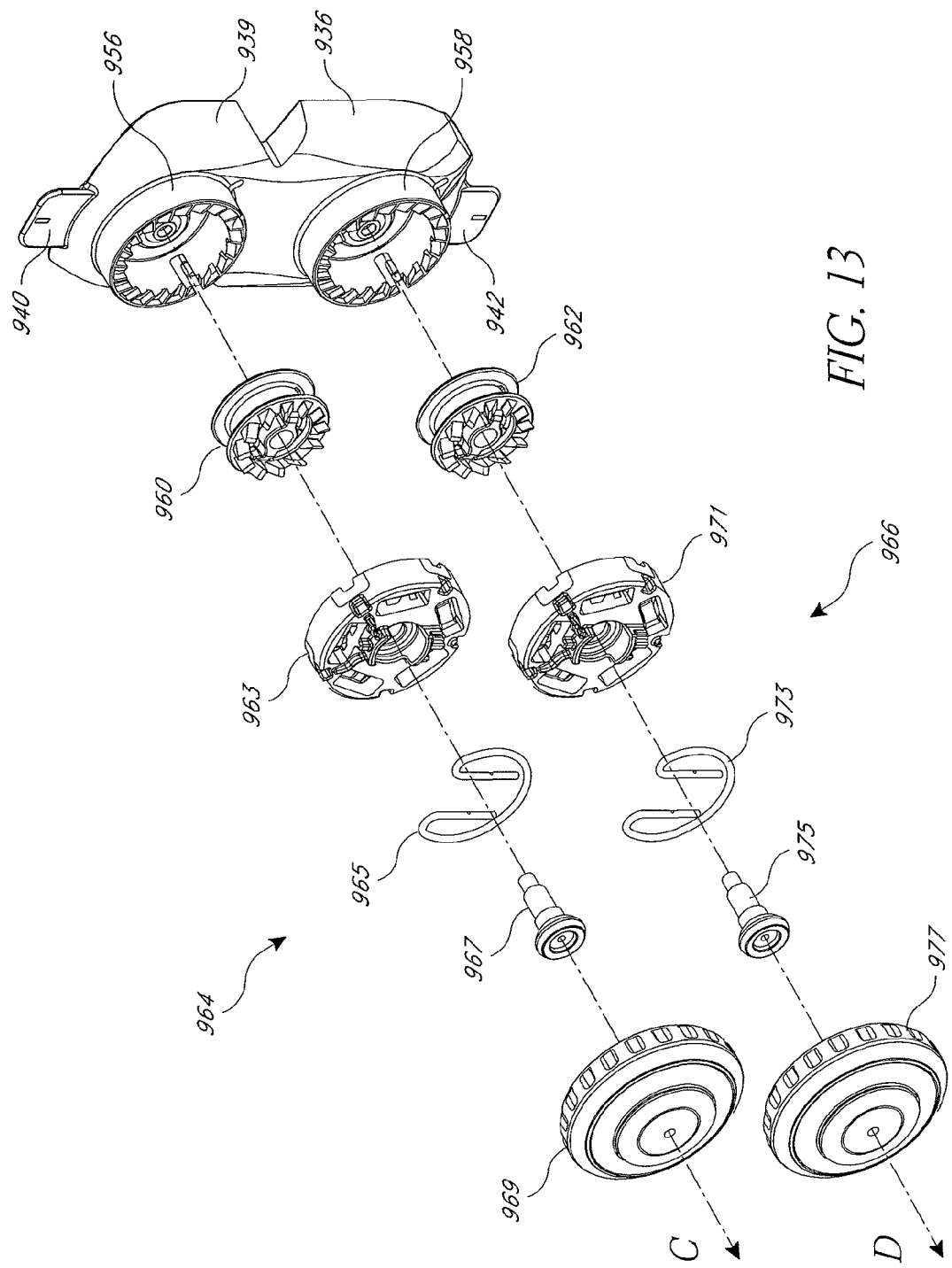
FIG. 13 is an exploded perspective view of the housing and the two reels.

FIG. 13 is an exploded perspective view of the housing piece 936 and reels 922, 924. The housing piece 936 can include an upper reel housing 956 configured to receive a first spool member 960 therein. A first knob 964 can engage the first spool member 960 and rotatably secure to the first reel housing 956. The first knob 964 can include a knob core 963, a knob spring 965, a knob bushing 967, and a knob cover 969. The housing piece 936 can also include a lower reel housing 958 configured to receive a second spool member 962 therein. A second knob 966 can engage the second spool member 962 and rotatably secure to the second reel housing 958. The second knob 966 can include a knob core 971, a knob spring 973, a knob bushing 975, and a knob cover 977. Additional details regarding the components and functionality of the reels 922, 924 of the illustrated embodiment are disclosed in the '013 application (at least at FIGS. 38A-46). It will be understood that various other types of reel or lace tightening mechanisms can be used in place of one or both the reel designs 922, 924 shown in the illustrated embodiment.

Mounting two reels 922, 924 substantially vertically onto a single housing piece 936 can allow the two reels 922, 924 to be located closer to each other than were each reel 922, 924 mounted onto a separate housing piece. In some embodiments, the brace 900 can be configured to be worn with a shoe over the top thereof. If the reels 922, 924 were placed too low, or too far apart so that they took up too much space on the back of the brace 900, the lower reel 924 could interfere with the shoe being worn over the top of the brace 900. Also, because the housing piece 936 forms an integrated, generally elongate, vertically oriented, rigid support on the back portion of the brace 900, the housing piece 936 provides better support to the brace 900 than would two housing pieces that each house one of the reels 922, 924.

The housing piece 936 can have a top stitch flange 940 and a bottom stitch flange 942 which can receive stitching 944, as shown in FIG. 10 to secure the housing piece 936 between an upper layer 946 and an underlying layer 948 of the brace 900. Alternatively, this stitch flange may be present around any portion of the periphery. Thus, a portion of the rigid housing piece 936 can be disposed under the upper layer 946 so as to be hidden from view. The reel housings 956, 958 can extend through holes formed in the upper layer 946 such that the reels 922, 924 can be mounted onto the external surface of the brace 100 where they can be visible and exposed.

Figure 14:
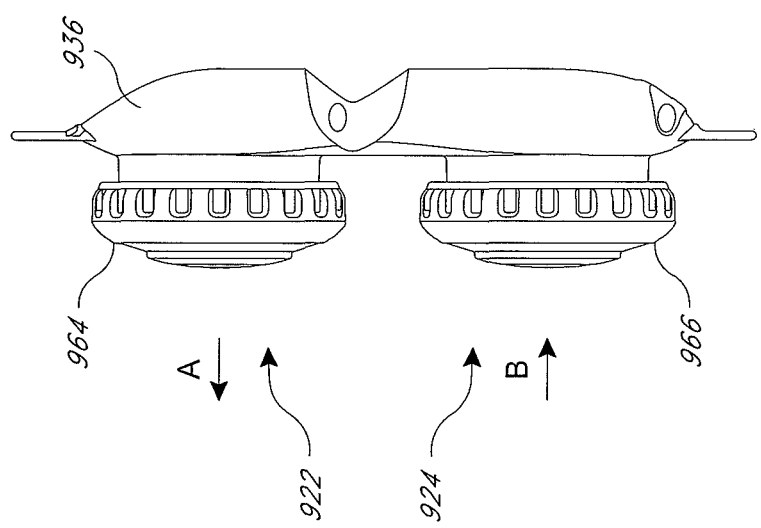
FIG. 14 is a side view of the housing and the two reels.

FIG. 14 is a side view of the housing piece 936 and the reels 922, 924. In some embodiments, the knobs 964, 966 can be toggled between an engaged position and a disengaged position. By pulling one of the knobs 964, 966 away from the housing piece 936 (in the direction of the arrow A), the knob 964, 966 can be disengaged such that the spool member 960, 962 is permitted to spin freely. Thus, when disengaged, the lace can be withdrawn from the reels 922, 924 such that the reels 922, 924 can be loosened. By pushing one of the knobs 964, 966 toward the housing piece 936, the knob 964, 966 can be toggled to the engaged position where the knob can only turn in the tightening direction to draw lace into the reels 922, 924.

Figure 15:
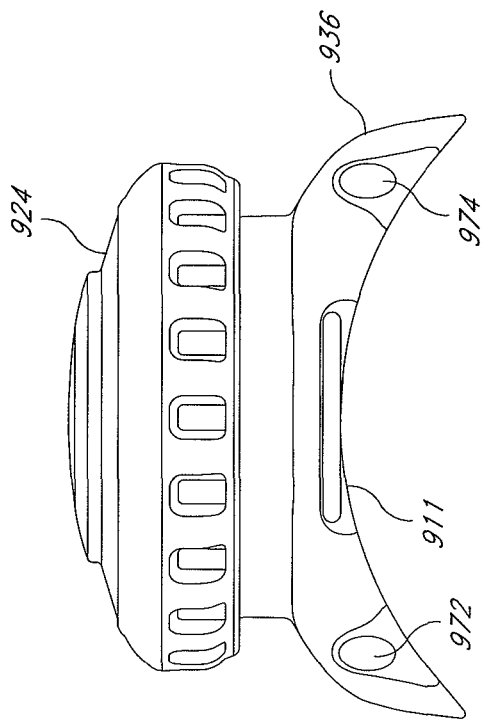
FIG. 15 is a bottom view of the housing and the lower reel.
Figure 16:
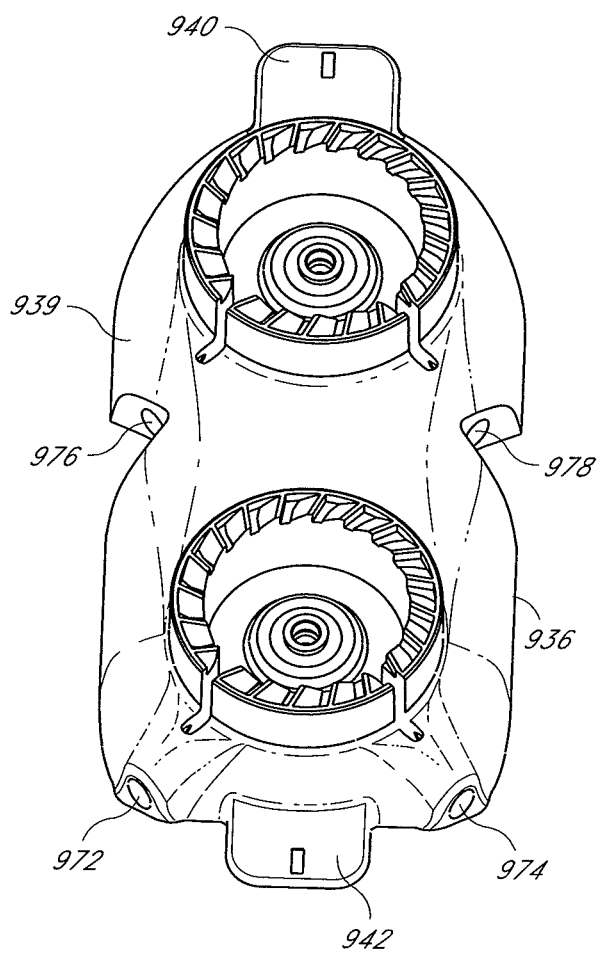
FIG. 16 is a perspective view of the housing.

FIG. 15 is a bottom view of the housing piece 936 and the reel 924. The back surface 911 of the housing piece 936 can be curved to conform to the curvature of brace 900 or approximate the curvature of the wearer's foot that is positioned nearest the back surface 911 of the housing piece 936. A first end of the lace 934 can enter the housing piece 936 via a hole 972, and a second end of the lace 934 can enter the housing piece 936 via the hole 974. The ends of the lace 934 can attach to the second spool member 962 such that when the reel 924 is rotated about a second axis D in the tightening direction the lace 934 is drawn into the reel 924 to tighten the lower portion 918 of the lace system 914. FIG. 16 is another perspective view of the housing member 936 that shows additional holes 976, 978 which can allow the ends of the lace 932 to enter the housing piece 936. The ends of the lace 932 can connect to the first spool member 960 such that when the reel 922 is rotated about a first axis C in the tightening direction, the lace 932 is drawn through the holes 176, 178 and into the reel 922 to tighten the upper portion 916 of the lacing system 914. In the illustrated embodiment, the axis C is substantially parallel to the axis D, which in some cases can allow the user to rotate both reels 922, 924 with generally the same hand motion without significant reorientation of the brace 900. Other, configurations are possible in which the axis C about which the first reel 922 rotates is not substantially parallel to the axis D about which the second reel 924 rotates. For example, the reels 922, 924 can be located on opposite sides of the brace 900.

In some embodiments the housing piece 936 can be made from a single material and can be a single unitary piece. In some embodiments, the housing piece 936 can be made from multiple materials that can have different properties, such as different levels of hardness. For example, in some embodiments, the main body 939 of the housing piece 396 can be made from a first material. The stitch flanges 940, 942 can be made from a second material, for example by overmolding, and can have a lower hardness than the first material such that the main body 939 can provide rigid support to the brace 900 while the stitch flanges 940, 942 can be soft enough to be punctured during the stitching process. In some cases, the main body 939 can be softer than the stitch flanges 940, 942 such that the body can be somewhat flexible to allow some degree of movement in the brace 900 while the stitch flanges 940, 942 can be harder to prevent them from being ripped from the stitching by the force of the tightened lacing system 914. The reel housings 957, 958 can also be made from a different material than the main body 939 or than the stitch flanges 940, 942.

Returning now to FIG. 9, the brace 100 can include several lace guides configured to provide lace paths for the laces 932, 934. Some of the lace guides can be closed back lace guides 926 which can prevent the lace from disengaging from the lace guides 926. In some embodiments, one or more of the lace guides can be a backless lace guide 928 (e.g., one of the lace guides of the upper portion 916 of the lace system). The lace 932 can be pulled out of the back of the backless lace guide 928 such that the lace 932 completely disengages from the backless lace guide 928. Once disengaged, the extra length of lace 932 that was previously engaged with the backless lace guide 928 can provide significant slack to the upper portion 916 of the lace system 914, thereby allowing the brace 900 to open wider to accommodate the insertion of the wearer's foot therein.

Once the user's foot is inserted, the lace 932 can be pulled back onto the backless lace guide 928 to take up the slack previously introduced. This allows the tightener (e.g., one or both of the reels 922, 924) to be smaller in that the lace length necessary to provide slack for inserting and removing the wearer's foot need not be stored inside the tightener.

Figure 17:
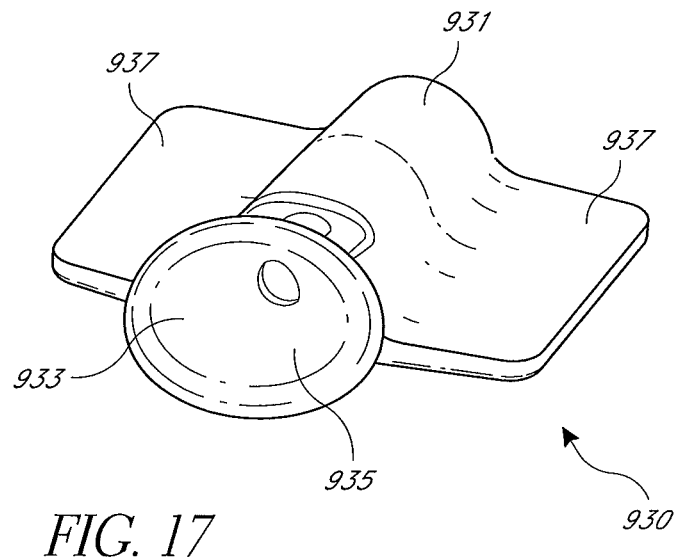
FIG. 17 is perspective view of a lace guide.

In some embodiments, one or more of the lace guides can direct the lace 932, 934 to the corresponding reels 922, 924. In some embodiments, the top two reel-leading lace guides 930a-b can lead the ends of the lace 932 to the upper reel 922 via tubing inserted into the lace guides 930a-b at the first end and inserted into the housing piece 936 at the second end, and the lower two reel-leading lace guides 930c-d can lead the ends of the lace 934, also via tubing, to the lower reel 924. FIG. 17 shows a perspective view of one of the reel-leading lace guides 930a-d. The reel-leading lace guide 930 can have a lace channel portion 931 that can be disposed below the upper layer 946 of the brace 900 such that the lace channel portion 931 is hidden from view during normal use. In some embodiments, the lace channel 931 can be longer than as shown in the illustrated embodiment and can lead to one of the reels 922, 924. In some embodiments, the lace channel 931 can lead to a supplemental channel, for example a polymer tube (not shown), that leads to the reels 922, 924. An end piece 933 can be positioned at least partially on the outside of the upper layer 946 such that the end piece 933 is exposed and visible. The end piece can have a non-uniform flange 935 around the opening to the lace channel that extends further at the bottom than at the top. The flange 935 can be generally bell-shaped. The end piece can provide a curved sliding surface for the lace 932, 934 to side against as it passes in or out of the lace channel. One or more stitch flanges 937 can be used to secure the lace guide 930 to the brace 900 with stitching, although other attachment methods can be used.

Figure 18:
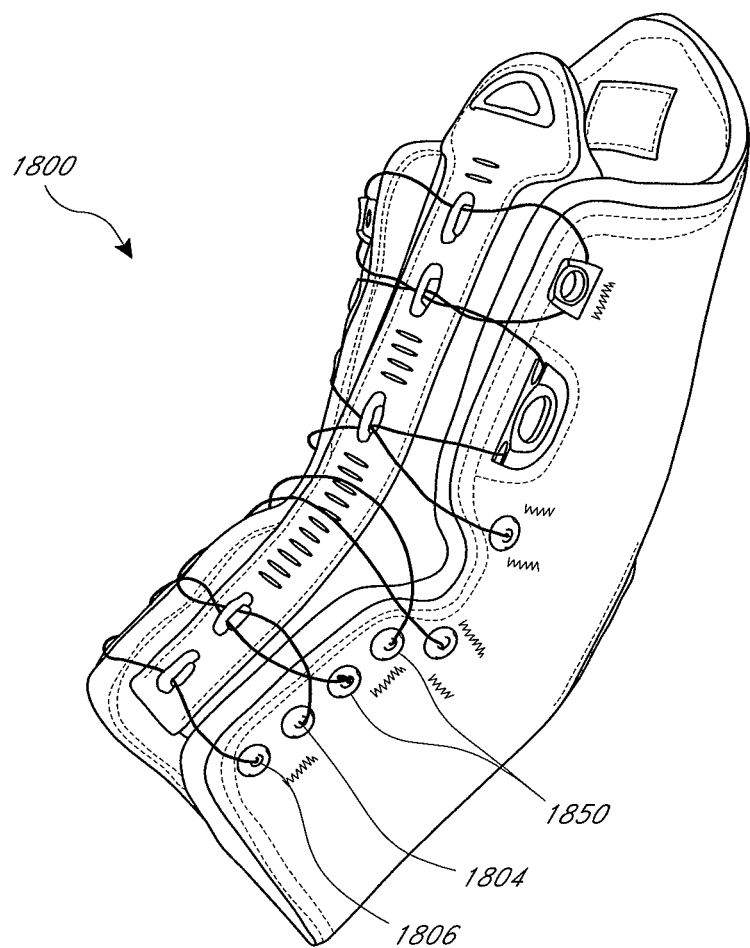
FIG. 18 is a perspective view of another embodiment of an ankle brace.

FIG. 18 is a perspective view of an ankle brace 1800 that can be similar to, or the same as, the ankle brace 900 discussed herein. In some embodiments, the brace 1800 can have included low profile lace guides 1850 that can be similar in some regards to the lace guides 930 discussed above. The lower profile lace guides can facilitate the use of the brace 1800 with a shoe worn over the top thereof. In some embodiments, each of the lace guides of the lower portion 1818 of the lace system 1814 can be low profile lace guides 1850.

Figure 19:
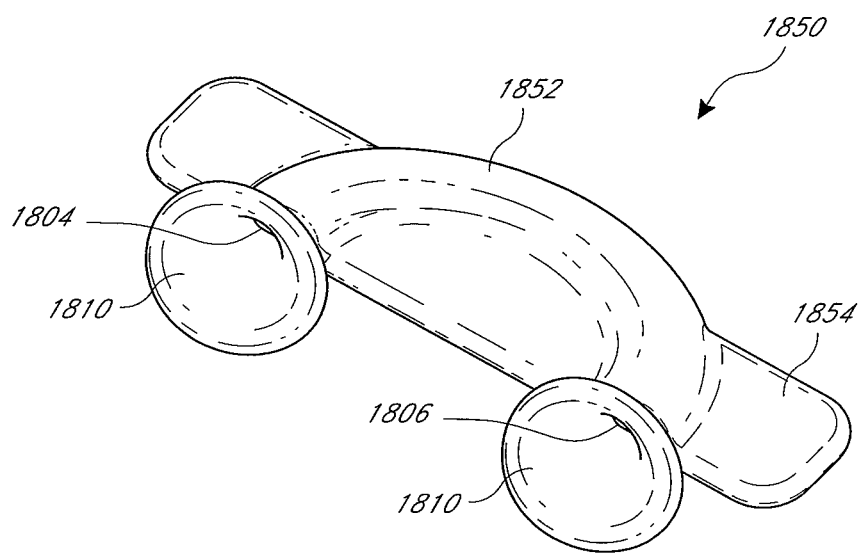
FIG. 19 is a perspective view of another lace guide.

FIG. 19 is a perspective view of a lower profile lace guide 1850 that includes a lace channel 1802 that can be disposed below an upper layer 1846 of the brace 1800 when assembled (as shown in FIG. 18). The lace guide 1850 can have a generally U-shaped lace channel 1852 with the lace passing from a first opening 1804 to a second opening 1806. The lace guide 1850 can include an end piece 1810 at each opening. The end piece 1810 can be similar to, or the same as the end piece 933 discussed above. A stitch flange 1852 can be used to stitch the lace guide 1850 to the brace 1800.

Figure 20:
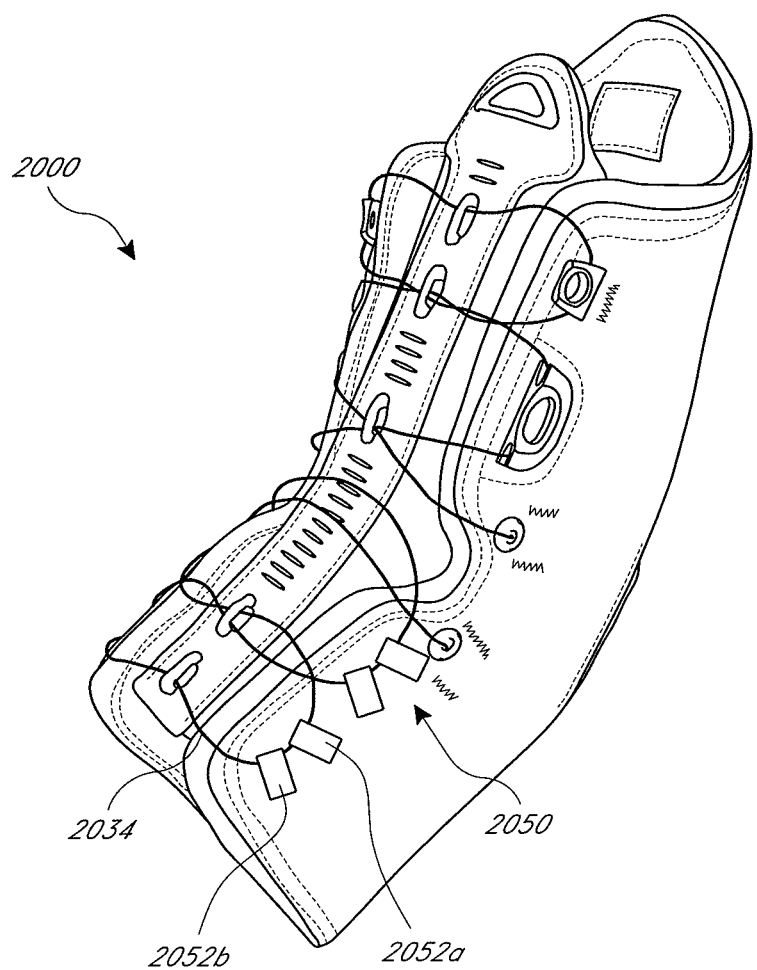
FIG. 20 is a perspective view of another embodiment of an ankle brace.

FIG. 20 is a perspective view of another embodiment of an ankle brace 2000 having low profile lace guides 2050. In some embodiments, one or more of the low profile lace guides 2050 can include a pair of angled loops 2052a, 2052b of, for instance, a woven polymer webbing, similar to the lace guides described in U.S. patent application Ser. No. 13/011,707 (the "'707 application"), filed Jan. 21, 2011, and titled "GUIDES FOR LACING SYSTEMS," the entirety of which is hereby incorporated by reference herein and made a part of this specification for all that it discloses. The lace 2034 can pass through two consecutive loops on one side before being directed to the opposite side, as described in greater detail in the '707 application. Other low profile lace guides can be used, such as, for example, those disclosed in connection with FIGS. 1-2B of the '707 application. The illustrated embodiment of FIG. 20 shows certain lace guides located on the lower portion of the brace 2000 having low profile lace guides 2050 (e.g., the angled loop pairs 2052a, 2052b), which can allow a shoe to be worn over the top of the brace 2000. As will be clear from the disclosure, low profile laces such as angled loop pairs similar to 2052a and 2052b can be used for the other lace guides on the brace 2000. For example, in some embodiments, all the lace guides on the brace 2000 can be low profile lace guides.

Figure 21:
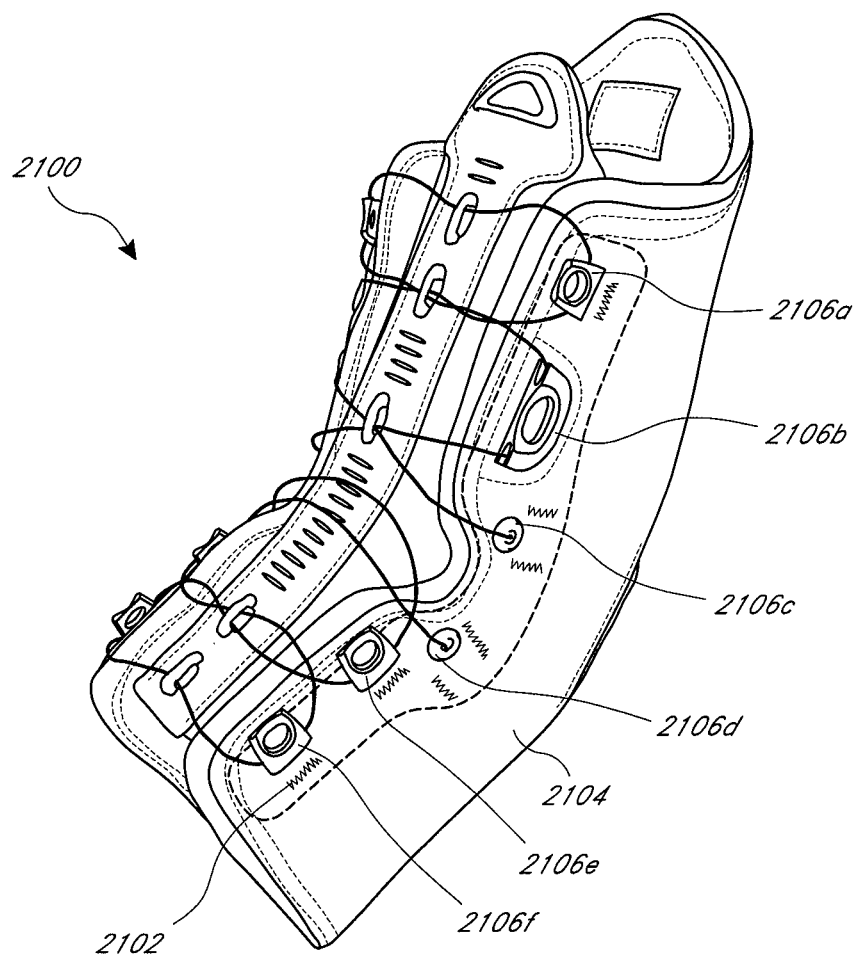
FIG. 21 is a perspective view of another embodiment of an ankle brace.

FIG. 21 is a perspective view of another embodiment of an ankle brace 2100 in which multiple lace guides are incorporated into a single housing piece. The single housing piece 2102 is shown in dotted lines in FIG. 21 because it is hidden from view below the upper layer 2104 of the brace 2100. In the illustrated embodiment, all six of the lace guides 2106a-f on the left side of the brace 2100 are incorporated into the single housing piece 2102, although in some embodiments a different number of lace guides 2106 can be incorporated into a single housing, and in some cases multiple housings can be used each incorporating multiple lace guides. For example, lace guides 2106a-c can be incorporated into one housing and the lace guides 2106d-f can be incorporated into a different housing. Many variations are possible. Joining multiple lace guides by a single housing piece can provide benefits similar to those discussed above in connection with the wrist brace 100. For example, the cost to manufacture the lace guides can be reduced if less pieces are required. Also, assembly of the brace 2100 can be simplified and the occurrence of erroneously positioned pieces can be reduced. Additionally, the housing piece can provide additional support and structure to the brace 2100 along with appropriate points of flexure.

While discussed in terms of certain embodiments, it should be appreciated that the disclosure is not so limited. The embodiments are explained herein by way of example, and there are numerous modifications, variations and other embodiments that may be employed that would still be within the scope of the present invention. Components can be added, removed, and/or rearranged both within certain embodiments and between embodiments. Additionally, processing steps may be added, removed, or reordered. A wide variety of designs and approaches are possible. Where numerical values and/or ranges are disclosed, other numerical values can also be used. For example, some embodiments can use numerical values that are outside the disclosed ranges.

For purposes of this disclosure, certain aspects, advantages, and novel features of embodiments of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:
1. A medical brace comprising:
a main body configured to be worn by a user; and
a lacing system configured to tighten and loosen the main body, the lacing system comprising:
a first reel configured to rotate about a first axis to tighten a first portion of the lacing system;

a second reel configured to rotate about a second axis different than the first axis to tighten a second portion of the lacing system; and a first unitary housing piece coupled to the body and configured to house and connect both the first reel and the second reel, wherein the medical brace is configured to restrict movement of a portion of the user anatomy.

2. The medical brace of claim 1, wherein the lacing system further comprises a plurality of lace guides mounted onto a second housing piece.

3. The medical brace of claim 2, wherein the second housing piece is substantially rigid and configured to provide substantially rigid support to the medical brace.

4. The medical brace of claim 2, wherein the first housing piece is substantially rigid and is configured to provide substantially rigid support to the medical brace, and wherein the medical brace does not include any rigid support member other than the first housing piece and the second housing piece.

5. The medical brace of claim 2, wherein the medical brace comprises a first side and a second side that are configured to be drawn together by tightening the lacing system, wherein the first reel and second reel are positioned on the first side of the medical brace, and wherein the plurality of lace guides are positioned on the second side of the medical brace.

6. The medical brace of claim 1, wherein the first housing piece is substantially rigid and is configured to provide substantially rigid support to the medical brace.

7. The medical brace of claim 6, wherein the medical brace does not include any rigid support member other than the housing piece.

8. The medical brace of claim 1, wherein the second reel is positioned adjacent to the first reel.

9. The medical brace of claim 1, wherein the medical brace is a wrist brace.

10. The medical brace of claim 1, wherein the medical brace is an ankle brace.

11. The medical brace of claim 1, wherein the first axis and the second axis are substantially parallel.

12. The medical brace of claim 1, wherein the first reel includes a first reel housing, the second reel includes a second reel housing, and wherein the first and second reel housing are coupled to or integral with the first housing piece.

13. The medical brace of claim 1, wherein at least a portion of the first housing piece comprises a material that is softer or harder than the reel.

14. A medical brace comprising:
a main body configured to be worn by a user; and
a lacing system configured to tighten and loosen the main body, the lacing system comprising:
a lace;
a plurality of lace guides configured to provide a lace path for the lace, wherein a first guide of the plurality of lace guides comprises a first opening and a second opening and a lace channel extending between the first opening and the second opening, wherein a second guide of the plurality of lace guides comprises a first opening, a second opening, and a lace channel extending between the first opening and the second opening, and wherein the second opening of the first guide and the first opening of the second guide are positioned between the first opening of the first guide and the second opening of the second guide;

a first reel configured to rotate about a first axis to tighten a first portion of the lacing system;

a second reel configured to rotate about a second axis different than the first axis to tighten a second portion of the lacing system;

a first unitary housing piece coupled to the body, and configured to house and connect both the first reel and the second reel; and a second unitary housing piece supporting the plurality of lace guides, wherein the medical brace is configured to restrict movement of a portion of the user anatomy.

15. The medical brace of claim 14, wherein the second housing piece is substantially rigid and is configured to provide substantially rigid support to the medical brace.

16. The medical brace of claim 15, wherein the first housing piece is substantially rigid and is configured to provide substantially rigid support to the medical brace, and wherein the medical brace does not include any rigid support member other than the first housing piece and the second housing piece.

17. The medical brace of claim 14, wherein the medical brace comprises a first side and a second side that are configured to be drawn together by tightening the lacing system, wherein the plurality of lace guides are positioned on the first side of the medical brace, and wherein no additional lace guides are positioned on the first side of the medical brace.

18. The medical brace of claim 14, wherein the plurality of lace guides are spaced apart from each other with portions of the second, unitary housing piece extending between the lace guides.

19. The medical brace of claim 14, wherein the plurality of lace guides are arranged generally linearly along a side of the medical brace.

20. The medical brace of claim 14, wherein the first reel includes a first reel housing, the second reel includes a second reel housing, and wherein the first and second reel housing are coupled to or integral with the first housing piece.

21. The medical brace of claim 14, wherein at least a portion of the first housing piece comprises a material that is softer or harder than the reel.

\* \* \* \* \*